(12) United States Patent
Berry

(10) Patent No.: US 11,304,843 B2
(45) Date of Patent: Apr. 19, 2022

(54) NON-INVASIVE URINARY AID

(71) Applicant: Kellen Wolfgang Daniel Berry, Hampton, VA (US)

(72) Inventor: Kellen Wolfgang Daniel Berry, Hampton, VA (US)

( * ) Notice: Subject to any disclaimer, the term of this patent is extended or adjusted under 35 U.S.C. 154(b) by 721 days.

(21) Appl. No.: 16/162,614

(22) Filed: Oct. 17, 2018

(65) Prior Publication Data

US 2020/0121491 A1 Apr. 23, 2020

(51) Int. Cl.
*A61F 5/455* (2006.01)

(52) U.S. Cl.
CPC .................. *A61F 5/4556* (2013.01)

(58) Field of Classification Search
CPC ...... A61F 5/455; A61F 5/4556; A61F 5/4408; A61B 10/007
USPC .......................................................... 4/144.3
See application file for complete search history.

(56) References Cited

U.S. PATENT DOCUMENTS

| | | | | |
|---|---|---|---|---|
| 4,023,216 A | * | 5/1977 | Li | A61F 5/4556 4/144.1 |
| 4,771,484 A | * | 9/1988 | Mozell | A61F 5/4556 4/144.4 |
| 5,893,176 A | * | 4/1999 | Magiera | A47K 11/12 4/144.4 |
| 2001/0037098 A1 | * | 11/2001 | Snyder | A61F 5/4553 604/331 |
| 2003/0149408 A1 | * | 8/2003 | Levinson | A61B 10/007 604/329 |
| 2005/0097662 A1 | * | 5/2005 | Leimkuhler | A61F 5/4556 4/144.3 |
| 2007/0191795 A1 | * | 8/2007 | Di Croce | A61F 5/4556 604/347 |
| 2009/0056003 A1 | * | 3/2009 | Ivie | A61F 5/4556 4/144.3 |
| 2010/0331798 A1 | * | 12/2010 | Block | A61F 5/4556 604/329 |
| 2015/0223784 A1 | * | 8/2015 | Van Damme | A61B 10/14507 73/864.63 |
| 2021/0236323 A1 | * | 8/2021 | Austermann | A61F 5/451 |

* cited by examiner

*Primary Examiner* — Nicholas J. Weiss
*Assistant Examiner* — Alessandro R Del Priore
(74) *Attorney, Agent, or Firm* — Patent Portfolio Builders PLLC

(57) ABSTRACT

The presented invention describes a noninvasive urinary aid for persons with vaginas. Which allows persons with vaginas to urinate without leaking, disrobing, or wiping, in a standing position. The urinary aids are manufactured of a pliable silicone and may be used repeatedly. When in use, the inlet opening is placed between the labia, pressed around the urethral opening to form a leak proof seal which creates a passage for urine excretion beyond the wearer's clothing. This ensures all urine is guided, via the urethral cup and connected tubing, to the location desired for disposal. The vulva, upon completion of urination, will not need to be dried.

4 Claims, 1 Drawing Sheet

NON-INVASIVE URINARY AID

BACKGROUND AND SUMMARY

The present invention generally relates to urinary devices, and more particularly relates to non-invasive urinary devices.

Many STP (Stand to Pee) portable urination devices are essentially funnels that share a similar shape and appearance. Typically, the funnel simply encompasses the vulva and directs urine out an exit spout, often resulting in urine leaking onto the wearer due either to insufficient seal, backsplash, or poor fluid dynamics. When the device manages to be successful the user's vulva is still left wet with urine deposits that require wiping.

Each unique urination attempt requires that the device either be adjusted, re-seated to ensure a seal, or even removed from a separate package and placed into the user's pants—an action that does not appear natural and requires varying levels of exposure.

The present invention is to provide a novel urinary device that results in a smooth and continuous urine stream consistent with the highest level of personal hygiene by eliminating any contact between the wearer's skin and the urine stream through a beveled elliptical inlet that surrounds the urethra and extends only slightly into the vaginal opening allowing the inlet to seal around the urethra. Unlike U.S. Pat. Nos. 4,198,979A, 4,911,698A, 4,568,339A, and 3,995,329A the elliptical cup is a smooth oval without divots and lays flat against the wearer. While the cup according to some embodiments does extend slightly into the vaginal opening it does not attempt to anchor within the vaginal canal. The shape and the design of these embodiment are intended to interact with the vaginal canal as little as possible, while the prior art is specifically inserted into the vaginal canal or has another opening for the purpose of stability and/or drainage.

Another advantage of the embodiments is the shape of the funnel itself. Unlike, U.S. Pat. Nos. 4,911,698A and 3,995,329A which have straight funnels which end at the exit tubes, the presented invention is comprised of both straight and curved walls which converge with the exit tube to increase fluid dynamics. This allows the funnel to adequately channel heavier urine streams. U.S. Pat. Nos. 4,198,979A, and 4,568,339A do have a curved section of the funnel that converges with the flat section of the funnel, however the curved section still ends at the exit tube so they do not present enhanced fluid dynamics.

Unlike all prior art mentioned, which have a straight exit tube that extend downwards between the legs, in the presented invention the exit tube is curved to allows the extension tubing to direct urine forward from the body reducing the chance of kinking when the tubing is pulled through the user's pants fly.

The presented invention is submitted with the claim that it improves upon various failures of prior art U.S. Pat. Nos. 4,198,979A, 4,911,698A, 4,568,339A, and 3,995,329A in both comfort, fluid dynamics, and stability without direct insertion into the vaginal canal or compression/encompassment of the outer labia. The presented invention is, furthermore, submitted as novel due to its unique aesthetic configuration. When all parts are considered there is a substantial difference in configuration that does not rely on the prior art's configuration apart from the basic use of geometric shapes.

I submit that the novel invention described herein is the culmination of my sole efforts to eliminate the need of adjustment with each urination attempt, concerns about leaking, and unhygienic conditions created by lack of ability to wipe.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The present invention is an apparatus that satisfies the above needs. A novel, non-invasive, urinary device is described that allows a person with a vagina to urinate in a standing position without requiring the removal of any clothing, resulting in a urination attempt that transfers no urine to the clothes nor leaves traces of urine between the labia.

In its final construction it will be a one-piece molded body comprising: a flattened cylindrical body that rests between the labia, a flat funnel with a beveled elliptical opening positioned around the urethra to prevent urine leakage that conforms and aligns with the back portion of the user's body creating a seal, and a curved section that converges with a silicone exit tube, such that the exit tube can be squeezed to break the vacuum that may occur as the tube is filled with urine.

Figure 1:
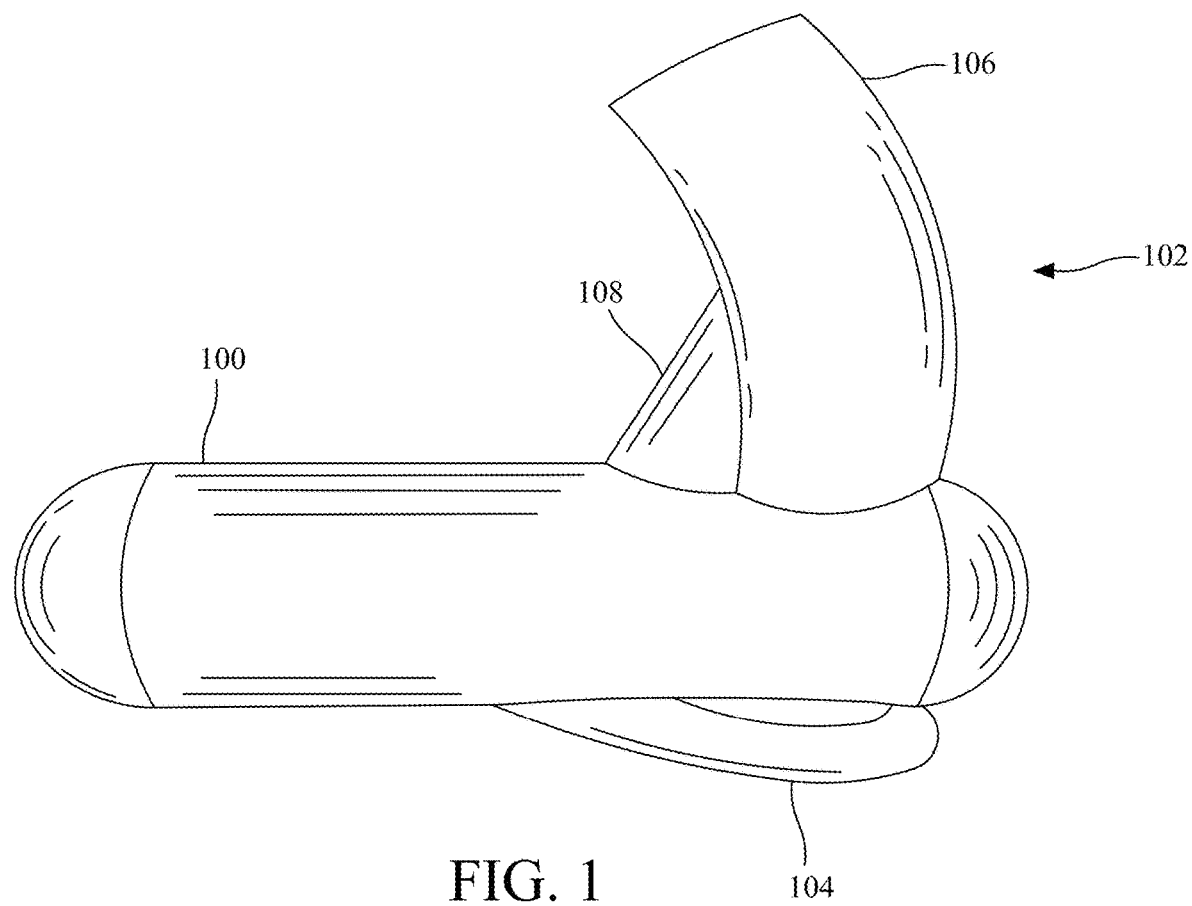
FIG. 1 depicts an embodiment.
Figure 2:
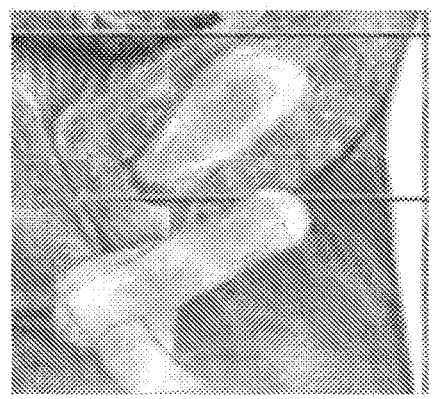
FIG. 2 is an illustration demonstrating placement of the invention.

The initial design was derived from a model created in TinkerCad and test models were cast in molds printed via a non-commercial model 3D printer. The device sits in the space between the inner labia, which, in conjunction with the outer labia, wrap around the uniquely shaped body to allow for maximum stability. A silicone tube (not shown in the Figures) exits the hole that points away from the urethra that faces slightly upward and forwards, pointing away from the user's body. FIG. 1 illustrates an embodiment.

Therein, a flattened cylindrical body 100 is shown, intersected by a small funnel 102. An elliptical opening 104 has been designed to be positioned around the urethral opening and is beveled to maximize comfort and seal. The elliptical shape allows for some variation in the placement of the urethra as well as encourages the fluid dynamics of the funnel 102. The funnel 102 that intersects the body 100 is shaped with a curved section 106 of the funnel 102 which is adapted to converge with the silicon exit tubing (not shown). The curved section 106 of the section of the funnel 102 and the flatter section 108 of the funnel 102 direct the urine for maximum flow and minimum backwards pressure. The exit portion 106 of the funnel 102 is both curved and flexible. The curve of the exit portion 106 allows inserted extension silicon tubing (not shown) to come forward and outwards from between the user's legs to minimize kinking if the tubing is pulled through the user's pants. By allowing the curved portion of the funnel 102 to converge with the exit tubing (not shown) the presented invention maximizes the fluid dynamics, allowing stronger urine streams without increased backsplash or backwards pressure by channeling the urine in two directions.

The described invention is inserted between the labia, placing the elliptical opening over and around the urethral sphincter. When seated correctly, the cylinder body will have the curved exit tubing pointing away from the body while the clitoris rests above the smooth cylindrical half of the upper portion of the cylinder body.

The present invention provides a novel urinary device that allows urination while standing with an absolute minimum of disrobing, adjustment, or wiping that remains firmly in place during a variety of movements to include running, biking, climbing, sitting, or other physical movements.

This is achieved through the unique flattened shape of the body which lies flat against the wearer. The rounded aspect of the body allows the labia to wrap around the device, securing it in place unlike patents: U.S. Pat. No. 4,198,979A which requires a harness to remain in place, U.S. Pat. No. 4,568,339A which encompasses the vulva and reaches to the anus, U.S. Pat. No. 3,995,329A which is squared with a panel that covers the labia Unlike the medicine spoon which also surrounds the urethra, the cylinder body of Spouti uses the vulva to hold the device in place so the wearer does not need to press the device into the tender flesh of the urethral sphincter achieve a seal. The elliptical shape is more conducive to creating a seal as it is not distorted by lateral pressure from the thighs. Due to the nature of the contact between the elliptical opening and the urethral sphincter the urine flows away from the body and without contacting the user's skin.

The invention claimed is:

1. A urinary device comprising:
   a cylindrical body having a closed first end and a closed second end, the cylindrical body being configured to rest between labia and to use a vulva to hold the device in place; and
   a funnel with a flat section having an opening configured to be positioned around the urethra to prevent urine leakage, wherein the opening is configured to conform and align with the vulva creating a seal, wherein the funnel intersects with and extends radially through the cylindrical body; and
   wherein the funnel has a curved section connected to the flat section and is adapted to converge with a silicone exit tube.

2. The urinary device of claim 1, wherein the urinary device is a one-piece molded device.

3. The urinary device of claim 1, wherein the opening is a beveled, elliptically-shaped opening.

4. The urinary device of claim 1, wherein the device is configured to use the vulva to hold the device in place, wherein the device does not require user interaction to maintain a seal during urination.

* * * * *